United States Patent [19]
Woods et al.

[11] Patent Number: 5,334,530
[45] Date of Patent: Aug. 2, 1994

[54] METHOD AND MEDIA FOR THE SOMATIC EMBRYOGENESIS AND REGENERATION OF BAMBOO

[76] Inventors: Susan H. Woods; John E. Woods, both of Rte. 2, Englewood, Tenn. 37329

[21] Appl. No.: 848,913

[22] Filed: Mar. 10, 1992

[51] Int. Cl.$^5$ ............................................. C12N 5/00
[52] U.S. Cl. ........................... 435/240.48; 435/240.1; 435/240.4; 435/240.49; 435/240.54
[58] Field of Search ............ 435/240.1, 240.4, 240.48, 435/240.49, 240.54

[56] References Cited

U.S. PATENT DOCUMENTS

| | | | |
|---|---|---|---|
| 4,000,951 | 8/1991 | Simpson | 435/240.4 |
| 4,548,901 | 10/1985 | Christianson et al. | 435/240.46 |
| 5,134,074 | 7/1992 | Gordon et al. | 435/240.4 |

FOREIGN PATENT DOCUMENTS

| | | | |
|---|---|---|---|
| 0328424 | 8/1989 | European Pat. Off. | 435/240.4 |
| 9000002 | 1/1990 | World Int. Prop. O. | 435/240.4 |

OTHER PUBLICATIONS

Huang, et al. (1988), Bot. Bull. Academia Sinica, 29:177–182, "Tissue Culture Investigations of Bamboo".

Rao, et al. (1985), Plant Cell Report, 4:191–194, "Somatic Embryogenesis and Regeneration of Plants in the Bamboo".

Yeh M.-L. and Chang, W.-C. (1987), Plant Science, 51:93–96, "Plant Regeneration Via Somatic Embryogenesis in Mature Embryo-Derived Callus . . . ".

Huang, et al. (1989), Bot. Bull. Academia Sinica, 30:49–57, "Tissue Culture Investigations of Bamboo".

Yeh. M.-L. and Chang, W.-C. (1986), Theor. Appl. Genet., 73:161–163, "Plant Regeneration Through Somatic Embyrogenesis in Callus Culture of Green . . . ".

*Primary Examiner*—Douglas W. Robinson
*Assistant Examiner*—Deborah K. Ware
*Attorney, Agent, or Firm*—Sherman and Shalloway

[57] ABSTRACT

The present invention provides a method and medium for the in vitro propagation of bamboo through organogenesis of vegetative explants from mature bamboo plants and somatic embryogenesis of the resulting organogenic callus. Optimal organogenesis is obtained by culturing vegetative explants from mature bamboo plants on first stage bamboo nutrient media comprising vitamins, MS salts, and supplemented with 1-naphthalemic acid, 6-benzylaminopurine and sucrose. Explants from the organogenic calli obtained from first stage media are cultured on second stage media (nutrient media comprising MS salts, vitamins, and supplemented with 2,4-dichlorophenoxyacetic acid, 6-benzylaminopurine and sugar) to induce somatic embryogenesis.

7 Claims, No Drawings

METHOD AND MEDIA FOR THE SOMATIC EMBRYOGENESIS AND REGENERATION OF BAMBOO

FIELD OF THE INVENTION

The invention relates to media formulation for the in vitro propagation of bamboo plants and efficient methods for the in vitro propagation of bamboo plants through somatic embryogenesis and organogenesis and liquid suspension culturing for the mass proliferation of somatic embryos.

BACKGROUND OF THE INVENTION

Bamboo is one of the most universally useful plant commodities known. Bamboo provides food, raw material, shelter and even medicine for the greater part of the world's population. However, information concerning the basic biology and reproduction of this complex and diverse group of plants lags behind that of other major agonomic plant species. Even the name bamboo is itself a vernacular term for more than 75 genera and 1250 species of the Gramineae (Soderstrom and Ellis, 1988 Smithsonian contribution No. 77), which are confused taxonomically as a result of their unusual flowering habits.

Once considered to be an inexhaustible source of raw material, bamboo is now threatened over a large area of the world. The "gregarious" flowering habit of bamboo, and the human population pressure disrupting the natural cycle of reforestation present an urgent need for the development of methods for large scale propagation of bamboo. Widely adaptable and efficient methods for vegetative propagation of bamboo on a commercial scale are not presently available. Bamboo could become an important new multipurpose tree crop in many areas where it has not been traditionally used, if reliable means of mass propagation were available. Another incentive for developing efficient mass propagation methods for bamboo is the increasing economic potential and aesthetic value of ornamental bamboos and grasses in the garden landscape (Reinhardt et al., 1989, Ornamental Grass Gardening; Friedman, N4 ).

Efficient in vitro propagation could prove to be a reliable and useful method for establishment of new bamboo plantations (Rao, et al. 1985, Plant Cell Report, 4:191–194). Rao, et al. demonstrated that it is possible to obtain somatic embryos from calli derived from cultured seeds of the bamboo, *Dendrocalamus strictus*. Only about 67% of the callus cultures formed well differentiated somatic embryos.

Similarly, Woods, et al. have accomplished somatic embryogenis in vitro from seeds of Mexican Weeping Bamboo (Woods, S., Phillips, G., Woods, J. and Collins, G., unpublished data). The efficiency of bamboo somatic embryogenesis was at least three times as efficient as that previously reported by Rao, et al., supra.

However, because bamboo rarely flowers and then flowers late in its life cycle there is a paucity of seed stores for bamboo. Thus, the establishment of parasexual alternatives to the use of seeds is necessary.

Somatic embryogenesis is now recognized as an acceptable method for plant propagation in vitro because it enables the rapid production of a large number of uniform plants within a relatively short period of time (Rao, et al., supra). The aseptic nature of regenerants formed in vitro is also useful in quarantine situations because such materials can be utilized for safe introduction of crops from one state or country to another.

The majority of research to date has been aimed at the development of shoot multiplication systems (Banik, R. L., 1987, in Rao, AN, et al. (eds), Proc. Internat. Bamboo Workshop, Hangzhov, 160–169; Manzur, MD., 1988, Agronomia 2: 14–19; Nadgauda, et al., 1990, Nature, 344: 335–336; Nadgir, et al., 1984, Silvae Genetica, 33: 219–223; Saxena, 1990, Plant Cell Reports, 9: 431–434. Plant regeneration via organogenesis from shoot apices was successful for four species (Huang, et al., 1989, Envir. Exp. Bot., 29: 307–315). There are only a few critical reports which deal with important economic bamboo species that provide significant contributions toward developing efficient protocols for somatic embryogenesis and plant regeneration. These include two reports of plants regenerated from floral structure explants (Yeh and Chang, 1986, Plant Cell Reports, 15:409–411; Yeh and Chang, 1986, Theor. App. Genet, 73: 161–163), and three reports of somatic embryogenesis and plant regeneration from seed explants (Yeh and Chang, 1987, Plant Sci., 51: 93–96; Mehta, et al. 1982, Proc 5th Internat. Cong. Plant Tissue Cell Culture, Fujiwara, Tokyo, 109–110; Rao, et al. 1985, supra). However, only one of these reports (Rao, et al., 1985) indicates potential as an efficient somatic embryogenesis system. A report of embryogenesis and plantlet regeneration from vegetative structures of green bamboo, *Phyllostachys viridis* (Hassan and Debergh, 1987, Plant Cell Tissue Organ Culture 10: 73–77), was followed later by a corrigendum indicating that the plant identified as green bamboo was incorrectly identified and was actually *Pogonatherum paniceum* (Lam) Hack., a grass (Hassan and Debergh, 1988, Plant Cell Tissue Organ Culture, 15: 93). Haploid plants obtained by androgenesis were reported recently for a bamboo species (Tsay, et al., 1990, Plant Cell Reports, 9: 349–351). Callus derived from vegetative structures was reported (Deckers, et al. In: Rao AN, et al. (eds) Proc. Internat. Bamboo Workshop, Hangzhou, 170–174; Huang, LC and Murasig T., 1982, Bot. Bull. Academia Sinica, 24: 31–52). Cell suspension and protoplast cultures have been investigated (Huang, et al., 1988, Bot. Bull. Academia Sinica, 29: 177–182; Huang, et al., 1989, Bot. Bull Academia Sinica, 30: 49–57).

Tissue culture of plants has primarily been concentrated on mature plant tissues for explants. Cells from mature tissues of some plants can be induced to multiply indefinitely in in vitro systems, to release free cells and small clumps of cells, and to produce somatic embryos from which normal plantlets can be generated. This concept recognizes that living mature plant cells are totipotent in that they retain in their nuclei the full genetic information of the zygotic nucleus and that the surrounding cytoplasm is capable of effectively carrying out the instructions from this genetic material. To date there have been no reports of successful culture and plant regeneration via somatic embryogenesis utilizing vegetative explants from mature bamboo plant parts. Such a means of mass propagation would make it possible to generate a large stock of uniform plants of selected bamboo species without the necessity of seeds.

SUMMARY OF THE INVENTION

In one aspect the present invention provides a method of regenerating bamboo plants by organogenesis and embryogenesis using tissue culture techniques. Tissue is excised from the bamboo plant and cultured under conditions to induce an organogenic callus from which plantlets are obtained. Vegetative explants from these organogenic calli or plantlets are cultured under conditions which induce somatic embryogenesis. The embryos may then be subcultured on germination medium whereby complete plants are obtained.

In another aspect of the invention, the somatic embryos are multiplied in liquid suspension cultures, thereby increasing the number of complete plants obtained from the original excised tissue.

The present invention also provides a medium capable of inducing somatic embryogenesis of an explant from a callus or plantlet obtained through organogenesis of a vegetative explant of a bamboo plant, whereby the number of embryos obtained is vastly multiplied.

In a preferred embodiment of the invention, the solid medium capable of inducing somatic embryogenesis is a nutrient medium supplemented with 2,4-dichlorophenoxyacetic acid, 6-benzylaminopurine and sugar.

A number of terms are known to have differing meanings when used in the literature. The following definitions are believed to be the ones most generally used in the field of botany and are consistent with the usage of the terms in the present specification.

"Callus" is generally considered to be a growth of unorganized and either unconnected or loosely connected plant cells generally produced from culturing an explant.

An "explant" is a piece of tissue taken from a donor plant for culturing.

A "plantlet" is a plant asexually reproduced by tissue culture.

"Somatic embryogenesis" is a process of embryo initiation and development from vegetative or non-gametic cells. The embryos from a given tissue source are presumed to be genetically identical.

An "organogenic callus" is a callus capable of forming only organ primordia. Organogenic calli develop shoots which must be subsequently induced to root in order to obtain complete plants. The offspring derived from an organogenic callus is not necessarily identical to the parent.

A "meristem" or "meristematic center" is a group of tissue forming cells capable of further development into plant organs, e.g., shoots and roots.

"Aseptic" is without infection or contaminating microorganisms.

DETAILED DESCRIPTION OF THE INVENTION

The present method utilizes a multistage culturing process for regenerating bamboo plants from vegetative explants of mature bamboo plants. In this process, an organogenic callus and plantlets are formed on a first stage semi-solid medium in order to obtain a stock of aseptic plants from which desired genotypes can be selected for explant material. Any suitable explant from tissue of the callus or plantlet is obtained and cultured on a second stage semi-solid medium capable of inducing callus formation and somatic embryogenesis. The somatic embryos may then be subcultured on germination medium and the resulting plants potted in soil.

The vegetative explants are obtained from mature bamboo plants. In a preferred embodiment, the explants are obtained from shoot apices or tips, however, any undifferentiated vegetative bamboo plant parts may be utilized. For example, tissue from leaf buds and meristematic centers for buds or roots may be used.

The first stage or induction medium will normally be a solid or semi solid nutrient medium which contains a balanced concentration of inorganic salts and organic nutrient materials, supplemented with plant growth hormones (auxins and cytokinins) and vitamins. Many such nutrient media are known and commercially available. For example, the stage one medium can contain Murashige and Skoog salts (MS), and i-inositol (100 mg/l), thiamine HCl (1 mg/l), nicotinic acid, (0.5 mg/l), pyridoxine HCl (0.5 mg/l), glycine (2 mg/l), 1-naphthaleneacetic acid (NAA) (about 1 mg/l), 6-benzylamino-purine (BA) (0.1-10 mg/l, preferably 0.5-3 mg/l), sugar (20-50 g/l), such as sucrose, and a gelling agent. The pH of the medium is adjusted from about 5.0 to about 6.0. Preferably, the pH of the first stage medium is 5.7. Auxins, such as NAA for example, are generally used in plant cell culture in a concentration of between 0.1-10 mg/l, more typically not exceeding about 3 mg/l. The particular auxin and its exact concentration will depend on the genera or species of bamboo being cultured. For example, Huang, et al. (1988), showed that 1 mg/l NAA is optimal for the induction of organogenic calli in *Bombusa multiplex*, whereas *Phyllostachys aurea* requires no NAA. The concentrations of auxins can be easily determined experimentally.

Culturing during this stage is normally carried out at about 25°–27° C. under about 12-20 hours daily exposure to light. Preferably, the cultures are maintained at 25° C. in 16 hours photoperiod of about 4.5 nEcm$^{-2}$ sec$^{-1}$ illumination.

Within 1 to 3 months of culturing with subculturing at approximately 4 week intervals the callus appears granular or nodular and is green. At about 2 to 6 months of culturing shoot primordia develop. These calli can be subcultured and maintained in culture for long periods of time. Calli with nodular green shoot primordia can be transferred to media with lower concentrations of or no growth regulators and will develop shoots which can be subsequently rooted and maintained in aseptic culture.

Explants from the organogenic calli and plantlets may be directly transferred to a second stage medium having sufficient concentrations of sugar, BA and 2,4-dichlorophenoxyacetic acid (2,4-D) to induce embryogenic callus formation and somatic embryos. The second stage medium is a solid or semi solid nutrient medium comprising a balanced concentration of inorganic salts and organic nutrient materials, supplemented with plant growth hormones and vitamins. The basal medium preferably contains Murashige and Skoog salts (MS), B5 vitamins, ascorbic acid, a gelling agent and is supplemented with 2,4-D, BA and sugar, preferably sucrose. The concentration of 2,4-D is preferably about 3 mg/l, but can vary from 0.5-6 mg/l. The optimal concentration may depend on the requirements of the particular bamboo species. The preferred concentration of BA is 0.5 mg/l but can vary from about 0.3-3 mg/l. Preferably the medium contains about 2%-5% sucrose, most preferably 2% sucrose, but other sugars can also be used. The concentrations of BA, 2,4-D and sucrose can each easily be adjusted for the particular species or genotype of bamboo. The pH of the medium is adjusted to about 5.6-6.0, preferably to 5.8.

The composition and use of the second stage medium is critical to the success of the present process. It differs significantly from the first stage medium by having a combination of BA and 2,4-D and lacking NAA. It is this specific combination of auxins, BA and sugar in the nutrient medium which induces embryogenesis from the organogenic callus explants, giving rise to multiple embryos from a single explant. A single explant can be multiplied, if desired, at least about 1,000-fold on stage two media and generally up to about 10,000-fold or more.

Explants from the organogenic calli from stage one media can be obtained from any tissue capable of undergoing embryogenesis on the second stage medium. Explants may be obtained, for example, from the leaf sheaths, internodes, roots and rhizomes of regenerated plantlets or organogenic calli from stage one media.

Culturing during the second stage is normally carried out at about 25°-27° C. in the dark or greatly subdued light, although albino plants have been generated in light. Preferably the cultures are maintained at 25° C. The resulting embryos are then transferred to a germination medium with an alternating light/dark photoperiod for development of plantlets. Germination media are generally basal media used at full to one-half strength in which growth regulators are greatly reduced or eliminated. Such media are commercially available, such as, for example Gamborg's B-5 medium (Gamborg, et al., 1968, Exp. Cell Res. 50: 151-158).

Somatic embryos obtained from the second stage medium are generally smooth, compact, shiny globular structures which develop into three basic types: an elongated club shape, an indented vase-shape and a convoluted disc-shape. The majority of plants develop from the vase-shaped embryos. The somatic embryos are bipolar, i.e. developing both root and shoot at germination.

Plants derived from the second stage medium can also be transferred to a soilless mix in covered containers for hardening, and then potted in soil for further growth.

In another aspect of the invention somatic embryos generated in the second stage medium are further multiplied in liquid suspension cultures. Although any liquid suspension culture capable of proliferating bamboo embryogenic callus tissue can be used, it is preferred to use one of two types of liquid suspension cultures. Type one utilizes clumps of proliferating globular calli and very little nonembryogenic tissues. This type of system has been used successfully with cotton and soybean (Finer, J. J., 1988, Plant Cell Tissue and Organ Culture, 15: 125-136).

The second type of preferred liquid suspension culture utilizes single cells or small clusters of cells of somatic embryos.

The embryogenic callus or cells are maintained and proliferated in liquid suspension cultures by recurrent selection of somatic embryos initiated from vegetative explants and maintained through stage 1 and stage 2 culturing protocols.

An embryogenic liquid suspension culture system for bamboo is worthwhile for selection work and is useful for genetic transformation utilizing microprojectile bombardment. Moreover, liquid suspension cultures enable the mass production of genetically identical plants. Because of the increased medium-to-tissue interface, selection systems will be improved in liquid suspension culture. Also, compared to tissue cultured on semisolid medium, the liquid suspension system will increase growth rate many times. Another advantage of liquid suspension culture is the production of large quantities of uniform embryogenic tissues for use as inocula for optimization of embryo regeneration. One of the most important and useful techniques of plant tissue culture is the isolation of protoplasts from cells and their culture. Embryogenic suspension has been shown to be a superior source of regenerable, transformable protoplasts.

Initiation, development and germination of embryos has been carried out on media, whereas the liquid suspension culture medium is useful for rapid uniform embryo proliferation.

EXAMPLE 1

Explants were obtained from the shoot tips of the secondary branches of mature plants of *Phyllostachys aurea, Bombusa multiplex* cv Alphonse Karr, and *Bombusa multiplex* cv Chinese Goddess. 10 replicates of each species were cultured on stage 1 medium consisting of:

| **MS salts | |
|---|---|
| i-inositol | 100 mg/l |
| thiamine HCl | 1 mg/l |
| nicotinic acid | 0.5 mg/l |
| pyridoxine HCl | 0.5 mg/l |
| glycine | 2 mg/l |
| NAA | 1 mg/l |
| BA | *x |
| sucrose | 30 g/l |
| Gelrite TM | 2 g/l |
| pH | 5.7 |

4 explants were cultured per plate at 25° C. in 16 hour photoperiod of light. The explants were subcultured at 4 week intervals and examined regularly for growth.

Visual examination showed that within 1-3 months the explants swelled and gave rise to nodular green calli. At 3-6 months shoot primordia and plantlets developed.

A small number, about 1000, plantlets were produced by the process.

| *x was 1 mg/l, 5 mg/l or 10 mg/l. | |
|---|---|
| **Murashige & Skoog Salt Base | |
| Components | mg/liter |
| $NH_4NO_3$ | 1650.000 |
| $KNO_3$ | 1900.000 |
| $CaCl_2$ (Anhydrous) | 333.000 |
| $MgSO_4$ (Anhydrous) | 181.000 |
| $KH_2PO_4$ | 170.000 |
| FeNaEDTA | 36.700 |
| $H_3BO_3$ | 6.200 |
| $MnSO_4.H_2O$ | 16.900 |
| $ZnSO_4.7H_2O$ | 8.600 |
| KCl | 0.8300 |
| $Na_2MoO_4.2H_2O$ | .250 |
| $CuSO_4.5H_2O$ | .025 |
| $CoCl_2.6H_2O$ | .025 |
| TOTAL | 4303.530 |

EXAMPLE 2

Explants obtained from the leaf sheath, internode, root and rhizome of plantlets regenerated from organogenic calli of *Phyllostachys aurea* (Golden Bamboo) cultured on first stage medium by the procedure in Example 1 were cultured on second stage medium. The second stage medium contained MS salts or Gamborg's B-5 medium supplemented with:

| Ascorbic Acid | 100.0 mg/l |
|---|---|

-continued

| | |
|---|---|
| BA | 0.5 mg/l |
| 2,4-D | 3 mg/l |
| sucrose | 20 g/l |
| Gelrite ™ | 2 g/l |
| pH | 5.8 |

The explants were maintained in the dark at 25° C. After 8–12 weeks of culturing 15–20 embryogenic callus clusters were recovered.

The efficiency of embryo multiplication was about 12%.

| *Gamborg's B-5 Medium | |
|---|---|
| Components | mg/liter |
| $(NH_4)_2SO_4$ | 134.000 |
| $H_3BO_3$ | 3.000 |
| $CaCl_2.2H_2O$ | 150.000 |
| $CoCl_2.6H_2O$ | .025 |
| $CuSO_4.5H_2O$ | .025 |
| $FeSO_4.7H_4O$ | 27.800 |
| $MgSO_4.7H_2O$ | 250.000 |
| $MnSO_4.H_2O$ | 10.000 |
| KCl | 0.750 |
| $KNO_3$ | 2500.000 |
| $Na_2EDTA$ | 37.300 |
| $Na_2MoO_4.2H_2O$ | 0.250 |
| $NaH_2PO_4.H_2O$ | 150.000 |
| $ZnSO_4.7H_2O$ | 2.000 |
| i-Inositol | 100.000 |
| Nicotinic Acid | 1.000 |
| Pyridoxine HCl | 1.000 |
| Thiamine HCl | 10.000 |

What is claimed is:

1. A process for regenerating bamboo plants from excised bamboo plant tissue which comprises the steps of
   (a) placing tissue obtained from mature undifferentiated vegetative bamboo plant parts on a first stage medium capable of inducing the excised tissue to produce an organogenic callus, said medium containing 1-naphthalene acetic acid, in an amount in the range of from 0.1 to 10 mg/l and culturing said excised tissue until an organogenic callus is obtained and
   (b) obtaining an explant from the organogenic callus of step (a),
   (c) transferring the explant obtained from step (b) to a second stage medium containing 6-benzylaminopurine in an amount in the range of from 0.3 to 3 mg/l and 2,4-dichlorophenoxy acetic acid, in an amount in the range of from 0.5 to 6 mg/l, said medium being capable of inducing callus formation and somatic embryogenesis of the callus,
   (d) cultivating a second callus, and
   (e) forming multiple embryos from the callus of step (d).

2. The process of claim 1 further comprising the step of subculturing the somatic embryos obtained from step (c) on germination medium capable of inducing embryo germination, whereby complete plants are obtained.

3. The process of claim 1 wherein said excised bamboo plant tissue is obtained from a shoot tip of a mature bamboo plant.

4. The process of claim 1 wherein said first stage medium further comprises mineral salts, vitamins, amino acids, a gelling agent, 6-benzylaminopurine (BA) in an amount in a range of from 0.1 to 10 mg/l, and sucrose, each in an amount sufficient to induce callus formation.

5. The process of claim 1 wherein the second stage medium further comprises mineral salts, vitamins, sucrose and a gelling agent, each in an amount sufficient to ensure somatic embryogenesis.

6. The process of claim 1 wherein the second stage medium comprises
   (i) about 3 mg/l 2,4-dichlorophenoxyacetic acid (2,4-D)
   (ii) about 0.5 mg/l 6-benzylaminopurine (BA), and
   (iii) about 2.0%–5.0% sucrose.

7. A process for regenerating bamboo plants from excised bamboo plant tissue, which comprises the steps of
   (a) placing excised tissue obtained from undifferentiated vegetative bamboo plant parts on a first stage medium capable of inducing the excised tissue to produce an organogenic callus, said medium containing 1-naphthalene acetic acid, in an amount in the range of from 0.1 to 10 mg/l, and culturing said excised tissue until an organogenic callus is obtained,
   (b) subculturing the organogenic callus of step (a) on medium containing 1-naphthalene acetic acid in an amount of from zero to less than 10 mg/l and less than the amount used in step (a) to obtain a second callus having shoots and roots,
   (c) maintaining said second callus having shoots and roots in aseptic culture to form a plantlet,
   (d) obtaining an explant from a leaf sheath, internode, root or rhizome of said plantlet,
   (e) transferring the explant from step (d) to a second stage medium containing 6-benzylaminopurine in an amount in the range of from 0.3 to 3 mg/l and 2,4-dichlorophenoxy acetic acid in an amount in the range of from 0.5 to 6 mg/l, said medium being capable of inducing callus formation and somatic embryogenesis of the callus,
   (f) cultivating the explant from step (e) to form a third callus and
   (g) forming multiple embryos from the third callus of step (f).

* * * * *